United States Patent [19]

Tanaka et al.

[11] Patent Number: 5,349,058

[45] Date of Patent: * Sep. 20, 1994

[54] NUCLEIC ACID ENCODING HUMAN MEVALONATE KINASE

[75] Inventors: Richard D. Tanaka, Yardley, Pa.; Beverly S. Ricci, Cranbury, N.J.; Stephen T. Mosley, Yardley, Pa.

[73] Assignee: E. R. Squibb & Sons, Inc., Princeton, N.J.

[ * ] Notice: The portion of the term of this patent subsequent to Apr. 10, 2007 has been disclaimed.

[21] Appl. No.: 475,577

[22] Filed: Feb. 6, 1990

[51] Int. Cl.$^5$ ............................................. C07H 17/00
[52] U.S. Cl. .................................. 536/23.2; 536/23.1; 536/23.5; 536/23.51; 930/240
[58] Field of Search ................... 536/27, 23.5, 23.1, 536/23.2, 23.51; 930/240

[56] References Cited

FOREIGN PATENT DOCUMENTS 221761 5/1987 European Pat. Off. .

OTHER PUBLICATIONS

P.N.A.S. vol. 87(8), p. 2872 Tanaka et al. see abstract print out.

Talk Schedule for the 1988 Aspen Hepatic Cholesterol and Lipoprotein Conference, Aspen, Colo., Aug. 18–21, 1988 "Regulation and Molecular Cloning of mevalonate kinase from rat liver".

Tanaka, R. D., et al., "The Regulation and Molecular Cloning of Mevalonate Kinase from Rat Liver", Arteriosclerosis 9, 717a (1989) & Circulation 80 (1989).

Tanaka, R. D. et al., "Purification and Regulation of Mevalonate Kinase from Rat Liver", J. Biol. Chem. 265, 2391–2398 (1990).

Flint, A. P. F., "The Activity and Kinetic Properties of Mevalonate Kinase in Superovulated Rat Ovary", Biochem. J. 120, 145–150 (1970).

Beytia, E. et al., "Purification and Mechanism of Action of Hog Liver Mevalonic Kinase", J. Biol. Chem. 245, 5450–5458 (1970).

Tchen, T. T., "Mevalonic Kinase: Purification and Properties", J. Biol. Chem. 233, 1100–1103 (1958).

Garcia-Peregrin, E. et al., "Isolation of Two Fractions with Mevalonate Kinase Activity from Pinus Pinaster and Agave Americana", FEBS Letters 30, 18–19 (1973).

Markley, K. et al., "Mevalonic Kinase in Rabbit Liver", Biochemica et Biophysica Acta 47, 327–335 (1961).

Loomis, W. D. et al., "Biosynthesis of Terpenes III. Mevalonic Kinase from Higher Plants", Biochemica et Biophysica Acta, 67, 54–63 (1963).

Williamson, I. P. et al., "The Formation of 5-Phosphomevalonate by Mevalonate Kinase in *Hevea brasilienisis* Latex" Biochem. J. 96, 862–871 (1965).

Garcia-Martinez, J. et al., "Revista Espanola de Fisiologia, ", 261–266 (1982), Partial Purification and Properties of Mevalonate Kinase from Neonatal Chick Liver.

Potty, V. H. et al., "Mevalonate-Activating Enzymes in the Orange", Phytochemistry 9, 99–105 (1970).

Goodfellow, R. D. et al., "Mevalonate Kinase from the Larva of the Fleshfly, Sarcophaga Bullata", Insect Biochem. 1, 271–282 (1971).

(List continued on next page.)

*Primary Examiner*—Margaret Moskowitz
*Assistant Examiner*—Bradley L. Sisson
*Attorney, Agent, or Firm*—Timothy J. Gaul

[57] ABSTRACT

Nucleic acid sequences, particularly DNA sequences, coding for all or a portion of human mevalonate kinase, expression vectors containing the DNA sequences, host cells containing the expression vectors, and methods for detecting the DNA sequences or the corresponding RNA sequences. The invention also concerns polypeptide molecules comprising all or a portion of human mevalonate kinase.

1 Claim, 3 Drawing Sheets

OTHER PUBLICATIONS

Gray, J. C. et al., "Mevalonate Kinase in Green Leaves and Etiolated Cotyledons of the French Bean *Phaseolus vulgaris*", Biochem, J. 133, 335–347 (1973).

Cooper, C. Z. et al., "Mevalonic Acid Kinase in *Euglena gracilis*", Plant Physiol. 42, 515–519 (1967).

Ness, G. C. et al., "Influence of Mevalonate Kinase on Studies of the MgATP-Dependent Inactivator of 3-Hydroxy-3-methylglutaryl Coenzyme A Reductase[1]", Archives of Biochemistry and Biophysics 214, 705–713 (1982).

Lee, C. S. et al., "An Improved Purification Procedure, an Alternative Assay and Activation of Mevalonate Kinase by ATP", Biochimica et Biophysica Acta. 747, 215–224 (1983).

Dorsey, J. K. et al., "The Inhibition of Mevalonic Kinase by Geranyl and Farnesyl Pyrophosphates", J. Biol. Chem. 243, 4667–4670 (1968).

Levy, H. R. et al., "Mevalonic Kinase and Phosphomevalonic Kinase from Liver", Biochem. J. 75, 417–428 (1960).

Porter, J. W., "Mevalonate Kinase", Methods in Enzymol., vol. 110, p. 71 (1985).

Popjak, G., "Enzymes of Sterol Biosynthesis in Liver and Intermediates of Sterol Biosynthesis", Methods in Enzymology, vol. 15, 393–455 (1969).

FIG.1A-1

```
 -91  CAAAACAAAAAGGTAGTGGGGAGCTGCTCCGGCTTCGGCGGGAGGCGGGAGGCGGGAGGCGGGAGGCGGGCAGGATTCCCAGGAGCC
   1  ATG TTG TCA GAA GTC CTA CTG GTG TCT GCT CCG GGG AAA GTC ATC CTT CAT GGA GAA CAT GCC GTG GTA   23
      MET Leu Ser Glu Val Leu Leu Val Ser Ala Pro Gly Lys Val Ile Leu His Gly Glu His Ala Val Val
  70  CAT GGC AAG GTA GCA CTG AGC TCC AGC GTA GTA TTG AAC TTG AGA ACA TTC CTC CGG CTT CAA CCC CAC AGC AAT   46
      His Gly Lys Val Ala Leu Ser Ser Ser Val Val Leu Asn Leu Arg Thr Phe Leu Arg Leu Gln Pro His Ser Asn
 139  GGG AAA GTG GAC CTC AGC TTA CCC AAC ATT GGT ATC AAG CGG GCC TGG GAT GTG GCC AGG CTT CAG TCA   69
      Gly Lys Val Asp Leu Ser Leu Pro Asn Ile Gly Ile Lys Arg Ala Trp Asp Val Ala Arg Leu Gln Ser
 208  CTG GAC ACA AGC TTT CTG GAG CAA GGT GAT GTC ACA ACA CCC ACC GAG CAA GTG CTG GAG AAG CTA AAG   92
      Leu Asp Thr Ser Phe Leu Glu Gln Gly Asp Val Thr Thr Pro Thr Glu Gln Val Leu Glu Lys Leu Lys
 277  GAG GTT GCA GGC TTG CCT GAC GAC TGT CGT GCT ACC GAG CGT GTG CTG GCC TTT CTT TAC TTA   115
      Glu Val Ala Gly Leu Pro Asp Asp Cys Arg Ala Thr Glu Arg Val Leu Ala Phe Leu Tyr Leu
 346  TAC CTG TCC ATC TGC AGG AAG CAG CGG GCC CTG CCG AGC GAT ATC GTA GTG TGG TCG GAG CTG CCC   138
      Tyr Leu Ser Ile Cys Arg Lys Gln Arg Ala Leu Pro Ser Asp Ile Val Val Trp Ser Glu Leu Pro
```

FIG.1A-2

```
415  CCC GGG GCG GGC TTG GGC TCC AGC GCC GCC TAC TCG GTG TGT CTG GCA GCA GCC CTC CTG ACT GTG TGC  161
     Pro Gly Ala Gly Leu Gly Ser Ser Ala Ala Tyr Ser Val Cys Leu Ala Ala Ala Leu Leu Thr Val Cys

484  GAG ATC CCA AAC CCG CTG AAG GAC GAT TGC GTC GTG ACC AAG TGG AGG AAC AAT GCT GAG CTA             184
     Glu Ile Pro Asn Pro Leu Lys Asp Asp Cys Val Val Thr Lys Trp Arg Asn Asn Ala Glu Leu

553  ATT AAC TGG AAG GCC TTC CAA GAG ATG ATT CAC GGG AGA GAC CCC TCC GGA GTG GTT GAC AAT GCT GTC     207
     Ile Asn Trp Lys Ala Phe Gln Glu Met Ile His Gly Arg Asp Pro Ser Gly Val Val Asp Asn Ala Val

622  AGC ACC TGG GGA GGA GCC TAC CGA CAT CAA GGG ATT TCA AAG TTA TCC AGG TCG CCA GCT CTC             230
     Ser Thr Trp Gly Gly Ala Tyr Arg His Gln Gly Ile Ser Lys Leu Ser Arg Ser Pro Ala Leu

691  CAG ATC CTG CTG ACC AAA GTC CCT CGC AAT ACC AGG GCC CTT GTG GCT GGC GTC AGA AAC AGG             253
     Gln Ile Leu Leu Thr Lys Val Pro Arg Asn Thr Arg Ala Leu Val Ala Gly Val Arg Asn Arg

760  CTG CTC AAG TTC CCA GAG ATC GTG GCC CTC ACA TCA ACC ATA GAT GCC ATC TCC CTG GAG TGT GAG         276
     Leu Leu Lys Phe Pro Glu Ile Val Ala Leu Thr Ser Thr Ile Asp Ala Ile Ser Leu Glu Cys Glu

829  GTG CTG GAG ATG GGG CCA CAG TAC CTC GTG GAA GAG CTC ATT GAC                                     299
     Val Leu Glu Met Gly Pro Gln Tyr Leu Val Glu Glu Leu Ile Asp

898  ATG AAC CAG CAC CAT CTG AAT GCC GGG GTG CTC CAC TCT GAC CTG TGC CAG GTG ACC                     322
     Met Asn Gln His His Leu Asn Ala Gly Val Leu His Ser Asp Leu Cys Gln Val Thr
```

FIG. 1B

```
 967 AGG GCC CGC GGA CTT CAC AGC AAG CTG ACT GGC GCA GGC GGT GGC TGT GGC ATC ACA CTC CTC AAG  345
     Arg Ala Arg Gly Leu His Ser Lys Leu Thr Gly Ala Gly Gly Gly Cys Gly Ile Thr Leu Leu Lys
1036 CCA GGG CTG GAG CAG CCA GAA GTG GCC ACG AAG CAG GCC CTG ACC AGC TGT GGC TTT GAC TGC TTG  368
     Pro Gly Leu Glu Gln Pro Glu Val Ala Thr Lys Gln Ala Leu Thr Ser Cys Gly Phe Asp Cys Leu
1105 GAA ACC AGC ATC GGT GCC CCC GGC GTC TCC ATC CAC CTG GAC AGC CGA GTC CAG CAA  391
     Glu Thr Ser Ile Gly Ala Pro Gly Val Ser Ile His Ser Ala Thr Leu Asp Ser Arg Val Gln Gln
1174 GCC CTG GAT GGC CTC TGA GAGGAGCCCACGACACTGCAGCCCCACCCAGATGCCCCTTTCTGGATTATTCTGGGGGCTGCAGTTC  396
     Ala Leu Asp Gly Leu
1259 GACTCTGTGCTGGCCAGCGAGGCCCAGTCCTGACACTGCTGGAGAGCCCCAGCCGCTTGGCGATGCCAGCCAAGCTCTGCAGTCCCAG
1350 CGGTGGGACCTAGGGAGGCATGGTCTGCCCTCTGGAGCCAGCGAGCAGGAGGTCCTCTGAGACTCCAGACC
1441 TGAGGGCGAGAAGGGCTGCTTCCCTGAAGCTCCCATCTGCTTCCCGGACCCCCCTGTCTCTCAGGGCCAGGCC
1532 CCAATGCTCAGGTGCTGGTTCCCGGTTCCCGGAGAAGTGCCTTCCTCTCTCCTTTCAGGGACCGGCACCTGCTGTCTGGGTGGCTCACTCAGCACTTGGTGT
1623 TCTCCCTCCTCCAGGAAGCCTTCCCTACCCCTTGTCGCCCCCAGGGGCTCCCCCAGGGCGTGGGGCCTGGTTAAATAAGGCAGGGTTTATATGCAC
1714 GGCCTTCCCTTCTACCTAGCGGGATGGGCTCCCCGAGGCGGTGGGCCTGGTTAAATAAGGCAGGGTTTATATGCAC
1805 TTTCTTCCGATCTGTACCTGAGAGGTTTGTGAAAAGATTTGTCAACAAAAA
```

NUCLEIC ACID ENCODING HUMAN MEVALONATE KINASE

BACKGROUND OF THE INVENTION

Mevalonate kinase (EC2.7.1.36; ATP: mevalonate-5-phosphotransferase) is a cytosolic enzyme in the cholesterol biosynthetic pathway which catalyzes the phosphorylation of mevalonate to form mevalonate-5-phosphate. Holloway, P. W. et al., Biochem J. 104, 57–70 (1967). Although mevalonate kinase has been described in animals and plants, very little is known about its regulation. However, there is some evidence to suggest that the regulation of mevalonate kinase may be involved in the regulation of cholesterol biosynthesis. The activity of mevalonate kinase is inhibited by geranyl pyrophosphate (GPP) and farnesyl pyrophosphate (FPP), which are intermediates in the cholesterol biosynthetic pathway after mevalonate kinase. GPP and FPP inhibit mevalonate kinase activity by binding competitively at the ATP-binding site on the enzyme, and it has been postulated that mevalonate kinase activity may be regulated by feedback inhibition from GPP and FPP. See, Dorsey, J. K. et al., J. Biol. Chem. 243, 4667–4670 (1968). However, further studies are needed to determine if mevalonate kinase plays a regulatory role in the cholesterol biosynthetic pathway.

Furthermore, mevalonic aciduria, a genetic disease involving the cholesterol biosynthetic pathway, has recently been discovered. There are six reported cases of mevalonic aciduria, and the genetic disease is transmitted as an autosomal recessive trait. Subjects with this disease have extremely high levels of mevalonate in their plasma and urine, and cells from these subjects have less than 10% of the normal levels of mevalonate kinase activity. Hoffman, G. et al., New Engl. J. Med. 314, 1610–1614, (1986); Brown, M. S. et al., J. Lipid Res. 21, 505–517 (1980). Mevalonic aciduria may result from a mutation in the gene coding for mevalonate kinase. However, additional studies are needed to clearly identify the mutation(s) responsible for this genetic defect.

Thus, it is readily apparent that the need exists in the art for sources of human mevalonate kinase so that its role in the regulation of cholesterol biosynthesis may be ascertained. There is also a need for methods for the detection and study of the human genetic disease mevalonic aciduria.

SUMMARY OF THE INVENTION

The present invention aids in fulfilling these and other needs in the art.

The present invention concerns a nucleic acid molecule comprising a nucleic acid sequence coding for all or a portion of human mevalonate kinase. Preferably, the nucleic acid molecule is a DNA (deoxyribonucleic acid) molecule, and the nucleic acid sequence is a DNA sequence. Further preferred is a DNA sequence having all or part of the nucleotide sequence substantially as shown in FIGS. 1A and 1B.

The present invention further concerns expression vectors comprising all or part of a DNA sequence coding for human mevalonate kinase. Preferably, the DNA sequence has all or part of the nucleotide sequence substantially as shown in FIGS. 1A and 1B.

The present invention additionally concerns prokaryotic or eukaryotic host cells containing an expression vector which contains all or part of a DNA sequence coding for human mevalonate kinase. Preferably, this DNA sequence has all or part of the nucleotide sequence substantially as shown in FIGS. 1A and 1B. The present invention also concerns methods for producing polypeptide molecules using these host cells.

The present invention further concerns methods for detecting nucleic acid sequences coding for all or a portion of human mevalonate kinase.

The present invention additionally concerns polypeptide molecules comprising all or a portion of human mevalonate kinase, said polypeptide molecules preferably having all or part of the amino acid sequence substantially as shown in FIGS. 1A and 1B.

The present invention also concerns methods for detecting or identifying agonists or antagonists to human mevalonate kinase.

BRIEF DESCRIPTION OF THE DRAWINGS

FIGS. 1A and 1B show the nucleotide sequence of the cDNA encoding human mevalonate kinase and the corresponding deduced amino acid sequence.

DETAILED DESCRIPTION OF THE INVENTION

The present invention concerns a nucleic acid molecule comprising a nucleic acid sequence coding for all or a portion of human mevalonate kinase. Preferably, the nucleic acid molecule is a DNA molecule and the nucleic acid sequence is a DNA sequence. Further preferred is a DNA sequence having all or part of the nucleotide sequence substantially as shown in FIGS. 1A and 1B, or a DNA sequence complementary to this DNA sequence. Additionally preferred are DNA molecules having DNA sequences which have greater than about 73% homology to the DNA sequence having all or part of the nucleotide sequence substantially as shown in FIGS. 1A and 1B. Also preferred are DNA molecules having DNA sequences which have greater than about 91% homology to the DNA sequence having all or part of the nucleotide sequence substantially corresponding to nucleotides 1–1188 as shown in FIGS. 1A and 1B.

The DNA sequences of the present invention may be isolated from a variety of sources, although the presently preferred sequence has been isolated from a human cDNA (complementary DNA) library. The exact amino acid sequence of the polypeptide molecule produced will vary with the initial DNA sequence.

The DNA sequences of the present invention may be obtained using various methods well-known to those of ordinary skill in the art. At least three alternative principal methods may be employed:

(1) the "isolation" of a double-stranded DNA sequence from genomic DNA which contains the sequence;

(2) the chemical synthesis of the DNA sequence; and (3) the in vitro synthesis of a double-stranded DNA sequence by enzymatic "reverse transcription" of mRNA (messenger RNA) encoded by the DNA sequence followed by isolation of the DNA sequence.

The last-mentioned method, which involves formation of a DNA complement of mRNA, is generally referred to as a cDNA method. One of the standard procedures for isolating a cDNA sequence of interest involves the preparation of plasmid-borne cDNA "libraries" derived from reverse transcription of mRNA molecules, some of which are encoded by the DNA sequence of interest.

These cDNA libraries may be prepared using various methods known in the art. For example, a double stranded cDNA copy of the mRNA is first generated using reverse transcriptase. After the formation of "sticky" ends (e.g., by digestion with a restriction endonuclease such as Eco RI), the double stranded cDNA with sticky ends is ligated to about a 2-fold molar excess of phage vector DNA, for example λgt10 or λgt11 DNA, which has also been digested with a restriction nuclease such as Eco RI to yield sticky ends, and phosphatased to prevent ligation without a cDNA insert. The ligation mixture is then packaged into infectious phage particles in vitro, and transformed into host bacteria. For λgt10 based libraries, a suitable host bacteria is *Escherichia coli* C600hf1A, while for λgt11 based libraries, a suitable host bacteria is *Escherichia coli* Y1088.

Once a cDNA library has been created, it must be screened to identify bacteriophage plaques or bacterial colonies containing the DNA sequence of interest.

Where substantial portions of the DNA sequence of interest are known, labeled single stranded DNA probe sequences duplicating a sequence putatively present in the "target" cDNA may be employed in DNA/DNA hybridization procedures carried out on cloned copies of the cDNA which have been denatured to single stranded form. If the cDNA library is to be screened in this manner, virtually any insertion vector, for example, λgt10, may be employed.

A cDNA library may also be screened for a cDNA of interest using immunoblotting techniques. If the library is to be screened in this manner, an appropriate *Escherichia coli* expression vector should be used. In one such approach, appropriate vectors are based on expression of a fusion protein in which a segment of the peptide of interest is fused to a highly expressed, stable *Escherichia coli* protein. For example, λgt11, which is an expression vector in which the cloned peptide coding sequences are fused to coding sequences for B-galactosidase, may be employed.

In one typical screening method suitable for either immunoblotting or hybridization techniques, the cDNA library is first spread out on agarose plates, and then the clones are transferred to filter membranes, for example, nitrocellulose membranes. A DNA probe may then be hybridized or an antibody may then be bound to the clones to identify those clones containing the cDNA of interest.

The DNA sequences of the present invention may be used in a variety of ways in accordance with the present invention. For example, they may be used as DNA probes to screen other cDNA or genomic DNA libraries to select by hybridization other DNA sequences that are related to human mevalonate kinase.

The DNA sequence of the present invention may also be used to prepare various mutations. Such mutations may be either degenerate, i.e., the mutation does not change the amino acid sequence encoded by the mutated codon, or non-degenerate, i.e., the mutation changes the amino acid sequence encoded by the mutated codon. Both types of mutations may be advantageous in producing or using the polypeptides of the present invention. For example, these mutations may permit higher levels of production, easier purification, or higher or lower mevalonate kinase activity.

The present invention further concerns expression vectors comprising all or part of a DNA sequence coding for human mevalonate kinase. The expression vectors preferably contain all or part of the DNA sequence having the nucleotide sequence substantially as shown in FIG. 1. Further preferred are expression vectors containing one or more control DNA sequences operatively linked to the DNA sequence coding for human mevalonate kinase. As used in this context, the term "operatively linked" means that the control DNA sequences are capable of directing the replication and/or the expression of the DNA sequence coding for human mevalonate kinase.

Expression vectors of utility in recombinant DNA techniques are often in the form of "plasmids", which refer to circular double stranded DNA loops which, in their vector form, are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

Expression vectors useful in the present invention typically contain an origin of replication, a promoter located in front of (i.e., upstream of) the gene to be expressed, the gene to be expressed, replication termination sequences and the remaining vector. The expression vectors may also include other DNA sequences known in the art, for example, stability leader sequences which provide for stability of the expression product, secretory leader sequences which provide for secretion of the expression product, regulatory sequences which allow expression of the structural gene to be modulated (e.g., by the presence or absence of nutrients in the growth medium), marking sequences which are capable of providing phenotypic selection in transformed host cells, and sequences which provide sites for cleavage by restriction endonucleases. The characteristics of the actual expression vector used must be compatible with the host cell which is to be employed. For example, when cloning in a mammalian cell system, the expression vector should contain promoters isolated from the genome of mammalian cells, (e.g., mouse metallothionien promoter), or from viruses that grow in these cells (e.g., vaccinia virus 7.5K promoter). An expression vector as contemplated by the present invention is at least capable of directing the replication, and preferably the expression, of the DNA sequences of the present invention. Suitable expression vectors into which DNA sequences of the present invention may be inserted are commercially available, and include those based on SV40-derived sequences, for example, pMAM, pMAMneo and EUK-C1, all of which may be obtained from Clontec Laboratories, Inc. in Palo Alto, Calif.

Particularly preferred is the expression vector designated pHMK1, described infra, which contains the DNA sequence coding for human mevalonate kinase, or expression vectors with the identifying characteristics of pHMK1.

Plasmid pHMK1 in an *Escherichia coli* host cell (strain DH5αF') was deposited with the American Type Culture Collection, Rockville, Md., on Jan. 23, 1990 under the Budapest Treaty and assigned ATCC accession no. 68208.

Suitable expression vectors containing the desired coding and control sequences may be constructed using standard recombinant DNA techniques known in the art, many of which are described in Maniatis et al., *Molecular Cloning: A Laboratory Manual*, Cold Spring Harbor Laboratory, Cold Spring Harbor, N.Y. (1982). Isolated plasmids or DNA fragments may be cleaved, tailored and religated to form the desired expression vector.

Cleavage of plasmids or DNA fragments may be performed, for example, by treating with one or more restriction enzymes under suitable reaction conditions. Suitable restriction enzymes are commercially available and include, for example, Bal I, Eco RI, Bam HI and Xho I. Suitable reaction conditions such as appropriate buffers, substrate amounts and reaction times and temperatures for a particular restriction enzyme are known in the art, and are generally specified by the manufacturer of the enzyme. In general, about 1 μg of a plasmid or DNA fragment is used with about 1 unit of enzyme in about 20 μl of buffer solution. Incubation times of about 1 hour at 37° C. are typical.

Tailoring of plasmids or DNA fragments may be performed by various methods known in the art. For example, if DNA molecules with blunt ends are required, the Klenow fragment of DNA Polymerase I may be employed. This enzyme is commercially available, and suitable reaction conditions are known in the art and are usually specified by the manufacturer. Treatment of a DNA preparation with about 10 units of Klenow fragment for about 15 minutes at about 15° C. is typical.

Ligation of plasmids or DNA fragments may also be performed by various methods known in the art. For example, DNA ligase from bacteriophage $T_4$ may be employed. This enzyme is commercially available, and suitable reaction conditions are known in the art and are usually specified by the manufacturer. Typically, equimolar amounts of the desired DNA molecules are treated with about 10 units of $T_4$ DNA ligase per 0.5 μg of DNA.

The present invention additionally concerns host cells containing an expression vector comprising all or part of a DNA sequence coding for human mevalonate kinase. The host cells preferably contain an expression vector containing all or part of the DNA sequence having the nucleotide sequence substantially as shown in FIGS. 1A and 1B. Further preferred are host cells containing an expression vector which contains one or more control DNA sequences capable of directing the replication and/or the expression of and operatively linked to a DNA sequence coding for human mevalonate kinase. Suitable host cells include both prokaryotic and eukaryotic cells. Suitable prokaryotic host cells include, for example, bacterial cells such as *Escherichia coli* and *Bacillus subtilis* cells. Suitable eukaryotic host cells include, for example, various mammalian cells such as COS cells, which are monkey kidey cells which express T antigen.

A particularly preferred bacterial host cell is *Escherichia coli* strain DH5αF', which may be obtained from BRL Life Technologies, Inc., Gaithersburg, Md.

Expression vectors may be introduced into host cells by various methods known in the art. For example, transfection of host cells with expression vectors may be carried out by the calcium phosphate precipitation method. However, other methods for introducing expression vectors into host cells, for example, electroporation, nuclear injection or protoplast fusion, may also be employed.

Once an expression vector has been introduced into an appropriate host cell, the host cell may be cultured under conditions permitting expression of large amounts of the desired polypeptide, in this case a polypeptide molecule comprising all or a portion of human mevalonate kinase. Such polypeptides are useful in the study of the characteristics of human mevalonate kinase, for example, its regulation and role in cholesterol biosynthesis. Such polypeptides may also be used to identify agonists and antagonists of human mevalonate kinase which may be potential cholesterol lowering drugs. The present invention therefore also concerns methods for detecting or identifying agonists or antagonists to human mevalonate kinase comprising contacting the agonist or antagonist with all or a portion of human mevalonate kinase, and determining the effect of the agonist or antagonist on the human mevalonate kinase. Preferably, the determined effect is the binding of the agonist or antagonist to or the resulting catalytic activity of the human mevalonate kinase.

Host cells containing an expression vector comprising all or part of a DNA sequence coding for human mevalonate kinase may be identified by one or more of the following four general approaches: (a) DNA-DNA hybridization; (b) the presence or absence of "marker" gene functions; (c) assessing the level of transcription as measured by the production of human mevalonate kinase mRNA transcripts in the host cell; and (d) detection of the gene product immunologically and/or by its catalytic activity.

In the first approach, the presence of a DNA sequence coding for human mevalonate kinase can be detected by DNA-DNA hybridization using probes complementary to the DNA sequence.

In the second approach, the recombinant expression vector host system can be identified and selected based upon the presence or absence of certain "marker" gene functions (e.g., thymidine kinase activity, resistance to antibiotics, etc.). For example, if a DNA sequence coding for human mevalonate kinase is inserted within a marker gene sequence of the expression vector, recombinants containing the DNA sequence coding for human mevalonate kinase can be identified by the absence of the marker gene function. Alternatively, a marker gene can be placed in tandem with the DNA sequence coding for human mevalonate kinase under the control of the same or a different promoter used to control the human mevalonate kinase coding sequence. Expression of the marker in response to induction or selection indicates expression of the DNA sequence coding for human mevalonate kinase.

In the third approach, the production of human mevalonate kinase mRNA transcripts can be assessed by hybridization assays. For example, polyadenylated RNA can be isolated and analyzed by Northern blotting using a probe complementary to the RNA sequence. Alternatively, the total nucleic acids of the host cell may be extracted and assayed for hybridization to such probes.

In the fourth approach, the expression of human mevalonate kinase protein can be assessed immunologically, for example, by Western blotting, or by the detection of catalytically active gene product. Where the host cell secretes the gene product, the cell free media obtained from the cultured transfected host cells may be assayed for mevalonate kinase enzyme activity. Where the gene product is not secreted, cell lysates may be assayed for such activity.

The DNA sequences of expression vectors, plasmids or DNA molecules of the present invention may be determined by various methods known in the art. For example, the dideoxy chain termination method as described in Sanger et al., Proc. Natl. Acad. Sci. USA 74, 5463–5467 (1977), or the Maxam-Gilbert method as described in Proc. Natl. Acad. Sci. USA 74, 560–564 (1977) may be employed.

It should, of course, be understood that not all expression vectors and DNA control sequences will function equally well to express the DNA sequences of the present invention. Neither will all host cells function equally well with the same expression system. However, one skilled in the art may make a selection among expression vectors, DNA control sequences, and host cells without undue experimentation and without departing from the scope of the present invention.

The present invention further concerns a method for detecting a nucleic acid sequence coding for all or a portion of human mevalonate kinase comprising contacting the nucleic acid sequence with a detectable marker which binds specifically to at least a portion of the nucleic acid sequence, and detecting the marker so bound. The presence of bound marker indicates the presence of the nucleic acid sequence. Preferably, the nucleic acid sequence is a DNA sequence having all or part of the nucleotide sequence substantially as shown in FIGS. 1A and 1B. Also preferred is a method in which the DNA sequence is a genomic DNA sequence. A DNA sample containing the DNA sequence may be isolated using various methods for DNA isolation which are well-known to those of ordinary skill in the art. For example, a genomic DNA sample may be isolated from tissue by rapidly freezing the tissue from which the DNA is to be isolated, crushing the tissue to produce readily digestible pieces, placing the crushed tissue in a solution of proteinase K and sodium dodecyl sulfate, and incubating the resulting solution until most of the cellular protein is degraded. The digest is then deprotenized by successive phenol/chloroform/ isoamyl alcohol extractions, recovered by ethanol precipitation, and dried and resuspended in buffer.

Also preferred is the method in which the nucleic acid sequence is an RNA sequence. Preferably, the RNA sequence is an mRNA sequence. An RNA sample containing the RNA sequence may be isolated using various methods for RNA isolation which are well-known to those of ordinary skill in the art. For example, an RNA sample may be isolated from cultured cells by washing the cells free of media and then lysing the cells by placing them in a 4M guanidinium solution. The viscosity of the resulting solution is reduced by drawing the lysate through a 20 gauge needle. The RNA is then pelleted through a $CsCl_2$ step gradient, and the supernatant fluid from the gradient carefully removed to allow complete separation of the RNA, found in the pellet, from Contaminating DNA and protein.

The detectable marker useful for identifying a nucleic acid sequence coding for all or a portion of human mevalonate kinase may be a labelled DNA sequence, including a labelled cDNA sequence, having a nucleotide sequence complementary to at least a portion of the DNA sequence coding for human mevalonate kinase.

The detectable marker may also be a labelled sense or antisense RNA sequence having a nucleotide sequence complementary to at least a portion of the DNA sequence coding for human mevalonate kinase.

The detectable markers of the present invention may be labelled with commonly employed radioactive labels, such as $^{32}P$, although other labels such as biotin may be employed. Various methods well-known to those of ordinary skill in the art may be used to label the detectable markers. For example, DNA sequences and RNA sequences may be labelled with $^{32}P$ using the random primer method.

Once a suitable detectable marker has been obtained, various methods well-known to those of ordinary skill in the art may be employed for contacting the detectable marker with the sample of interest. For example, DNA-DNA, RNA-RNA and DNA-RNA hybridizations may be performed using standard procedures known in the art. In a typical DNA-DNA hybridization procedure for detecting DNA sequences coding for all or a portion of human mevalonate kinase in genomic DNA, the DNA is first isolated using known methods and then digested with one or more restriction enzymes under suitable reaction conditions. The resulting DNA fragments are separated on agarose gels and denatured in situ. The fragments are then transferred from the gels to nitrocellulose filters where they are immobilized. After prehybridization to reduce nonspecific hybridization, the desired radiolabeled nucleic acid probe is hybridized to the immobilized DNA fragments. The filter is then washed to remove unbound and weakly bound probe, and is then autoradiographed.

The presence of bound detectable marker may be detected using various methods well-known to those of ordinary skill in the art. For example, if the detectable marker is radioactively labelled, autoradiography may be employed. Depending on the label employed, other detection methods such as spectrophotometry may also be used.

The presence in a human sample, for example a tissue sample, of low levels of a nucleic acid sequence coding for human mevalonate kinase may be indicative of the genetic disease mevalonic aciduria.

The present invention further concerns polypeptide molecules comprising all or a portion of human mevalonate kinase, said polypeptide molecules preferably having all or part of the amino acid sequence substantially as shown in FIGS. 1A and 1B. Also preferred are polypeptide molecules which are catalytically active (i.e., possess mevalonate kinase enzyme activity). Particularly preferred are polypeptide molecules corresponding to the catalytic site of human mevalonate kinase. Additionally preferred are polypeptide molecules having amino acid sequences which have greater than about 83% homology to all or part of the amino acid sequence substantially as shown in FIGS. 1A and 1B.

All amino acid residues identified herein are in the natural L-configuration. In keeping with standard polypeptide nomenclature, *J. Biol. Chem.*, 243:3557–59 (1969), abbreviations for amino acid residues are as shown in the following Table of Correspondence:

| TABLE OF CORRESPONDENCE | | |
| --- | --- | --- |
| SYMBOL | | |
| 1-Letter | 3-Letter | AMINO ACID |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |

TABLE OF CORRESPONDENCE -continued

| SYMBOL | | |
|---|---|---|
| 1-Letter | 3-Letter | AMINO ACID |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Try | L-tryptophan |
| R | Arg | L-arginine |
| D | Asp | L-aspartic acid |
| N | Asn | L-asparagine |
| C | Cys | L-cysteine |

All amino acid sequences are represented herein by formulas whose left to right orientation is in the conventional direction of amino-terminus to carboxy-terminus.

The polypeptides of the present invention may be obtained by synthetic means, i.e., chemical synthesis of the polypeptide from its component amino acids, by methods known to those of ordinary skill in the art. For example, the solid phase procedure described by Houghton et al., *Proc. Natl. Acad. Sci.* 82:5135 (1985) may be employed. It is preferred that the polypeptides be obtained by production in prokaryotic or eukaryotic host cells expressing all or part of a DNA sequence coding for human mevalonate kinase, or by in vitro translation of the mRNA encoded by all or part of the DNA sequence coding for human mevalonate kinase. Techniques for the production of polypeptides by these means are known in the art, and are described herein.

The polypeptides of the present invention may be isolated and purified to some degree using various protein purification techniques. For example, chromatographic procedures such as ion exchange chromatography, gel filtration chromatography and immunoaffinity chromatography may be employed.

The polypeptides of the present invention may be used in a wide variety of ways. For example, the polypeptides may be used to prepare in a known manner polyclonal or monoclonal antibodies capable of binding the polypeptides. These antibodies may in turn be used for the detection of the polypeptides of the present invention in a sample, for example, a cell or tissue sample, using immunoassay techniques, for example, radioimmunoassay or enzyme immunoassay. The antibodies may also be used in affinity chromatography for purifying the polypeptides of the present invention and isolating them from natural sources.

The polypeptides of the present invention have been defined by means of determined DNA and deduced amino acid sequencing. Due to the degeneracy of the genetic code, other DNA sequences which encode the same amino acid sequence as depicted in FIGS. 1A and 1B may be used for the production of the polypeptides of the present invention. In addition, it will be understood that allelic variations of these DNA and amino acid sequences naturally exist, or may be intentionally introduced using methods known in the art. These variations may be demonstrated by one or more amino acid differences in the overall sequence, or by deletions, substitutions, insertions, inversions or additions of one or more amino acids in said sequence. Such amino acid substitutions may be made, for example, on the basis of similarity in polarity, charge, solubility, hydrophobicity, hydrophilicity and/or the amphiphathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine; glycine, alanine; asparagine, glutamine; serine, threonine; phenylalanine, tyrosine. All such variations are included within the scope of the present invention.

The following examples are further illustrative of the present invention. These examples are not intended to limit the scope of the present invention, and provide further understanding of the invention.

EXAMPLE 1

Materials

Lactate dehydrogenase, pyruvate kinase, phosphoenolypyruvate, dithiothreitol (DTT), NADH and ATP were purchased from Boehringer Mannheim Biochemicals (Indianapolis, Ind.). RS-mevalonic acid lactone (a mevalonate kinase substrate), leupeptin, ADA (N-[2-acetamido]-2-iminodiacetic acid) buffer, ATP-agarose beads (linked through the $N^6$-amino group), 2-mercaptoethanol, cholesterol, cholic acid and gel filtration molecule weight markers were from Sigma Chemical Co. (St. Louis, Mo.). Blue Sepharose, Protein-A Sepharose CL-4B, Sephacryl S-200 and Sephadex G-150 were from Pharmacia LKB Biotechnology Inc. (Piscataway, N.J.). Acrylamide, ammonium persulfate, N,N,N',N'-tetramethylethylenediamine molecular weight standards and silver staining kits were purchased from BioRad Labs (Richmond, Calif.). All reagents were of analytical grade quality. $^{125}$I-Protein A was from Amersham Corp. (Arlington Heights, Ill.) and $^{14}$C-labelled molecular weight standards were from BRL Life Technologies, Inc. (Gaithersburg, Md.). Pravastatin and lovastatin (mevinolin) were from E. R. Squibb and Sons, Inc. and Sankyo, Ltd. (Japan), respectively, and cholestyramine (Questran) was purchased from Bristol Laboratories (Wallingford, Conn.). Farnesyl pyrophosphate was prepared according to the method of Davisson et al., Methods Enzymol 110, 130-144 (1985).

EXAMPLE 2

Mevalonate Kinase Assay

Mevalonate kinase activity was measured using a spectrophotometric assay as described by Popjak, G., Methods Enzymol. 15, 393-453 (1969). The reaction mixture for the assay contained 100 mM potassium phosphate buffer (pH 7.0), 10 mM KF, 10 mM $MgCl_2$, 10 mM DTT, 0.5 mM NADH, 1 mM phosphoenolypyruvate, 2 mM ATP, 20 units of pyruvate kinase, 27 units of lactate dehydrogenase and 3 mM RS-mevalonate, a mevalonate kinase substrate. Final volume of the reaction mixture was 1 ml. Enzyme assays were conducted at 25° C. on a Perkin Elmer Lambda 3B dual-beam spectro-photometer. The background rate of NADH oxidation was measured for 60 seconds, then mevalonate was added and the reaction rate was measured for an additional 60 seconds. One unit of enzyme activity was defined as the amount of activity required to produce 1 $\mu$mol of mevalonate-5-phosphate per minute. Enzyme activity measured in the spectro-photometric assay was proportional to the amount of protein in the assay up to a final concentration of approximately 200 µg/ml. Protein concentration was determined by the method of Bradford, M., Anal. Biochem. 72, 248-254 (1976).

EXAMPLE 3
DNA Sequencing

DNA sequences were determined using the dideoxy-chain termination method of Sanger, F. et al., Proc. Natl. Acad. Sci. USA 74, 5463-5467 (1977). Sequencing reactions using the Klenow fragment of DNA polymerase I (New England Biolabs, Beverly, Mass.) or modified T7 DNA polymerase (Sequenase, United States Biochemicals, Cleveland, Ohio) were performed following the manufacturer's protocol. DNA sequences were aligned using the Intelligenetics computer program, and the EMBL/GenBank and PIR data bases were searched for homologous DNA and protein sequences.

EXAMPLE 4
Purification of Rat Mevalonate Kinase

Female Sprague-Dawley rats (80 g body weight, CAMM Laboratories, Wayne, N.J.) were acclimated to a 12 hour light/12 hour dark cycle for 14 days. After acclimation, the rats (n=7) were treated for 15 days with a diet containing 5% cholestyramine and 1% pravastatin, and then they were sacrificed at the last hour of the dark cycle. The livers were quickly excised and homogenized in 1.5 volumes of ice-cold buffer A (0.1M sucrose, 50 mM KCl, 30 mM dipotassium EDTA, 10 mM DTT, 0.1 mM leupeptin and 40 mM potassium phosphate buffer, pH 7.2) using a glass, Potter-Elvejhem homogenizer with a motor driven teflon pestle. Liver homogenates were centrifuged at 10,000×g for 10 minutes at 5° C., and the supernates were collected and recentrifuged under identical conditions. The supernates were then centrifuged at 100,000×g for 45 minutes at 5° C. The 100,000×g supernates were collected and kept at 0° C., saturated ammonium sulfate (pH 7.4) was slowly added to a final concentration of 45%, and the precipitate was collected by centrifugation at 17,500×g for 15 minutes at 5° C. After decanting the supernate, the pellet was dissolved in buffer B (10 mM DDT and 20 mM Tris, pH 7.5) and then centrifuged at 19,000×g for 60 minutes at 5° C. The supernate was collected and loaded onto a Blue Sepharose column (2.5×10 cm) which was equilibrated with buffer B at room temperature. Unbound material was removed by washing with 60 ml of buffer B and then approximately 500 ml of buffer B containing 0.1M KCl. Mevalonate kinase activity was eluted from the column using a linear salt gradient of 0.1M to 1M KCl in buffer B. Fractions which contained enzyme activity were pooled and the enzyme was precipitated with 60% ammonium sulfate (pH 7.4). The precipitate was collected by centrifugation at 17,500×g for 15 minutes at 5° C., the pellet was dissolved in buffer C (10 mM DTT and 20 mM ADA, pH 7.0) and centrifuged at 19,500×g for 45 minutes at 5° C. The supernate was collected and loaded onto a Sephadex G-150 column (2.5×44.5 cm) which was equilibrated and washed in buffer C at room temperature. Fractions containing mevalonate kinase activity were pooled and loaded directly onto an ATP-agarose column (1.5×4.5 cm) which was equilibrated with 10 mM DTT (pH 7.0) at room temperature. The column was washed with 10 mM DTT, and then the enzyme was eluted with 10 mM DTT containing 15 µM FPP. Potassium phosphate (pH 7.0) was added to each column fraction to yield a final concentration of 0.1M. The fractions containing mevalonate kinase activity were collected and stored at 5° C. The above purification procedure is summarized in Table 1.

The rat mevalonate kinase so purified appeared homogeneous, since only one protein-staining band (silver staining) was observed after the enzyme was electrophoreses on SDS-polyacrylamide gels, and only one protein-staining band (silver staining) was observed after isoelectric focusing.

After purification, the enzyme was stable for several months when stored at 5° C. in buffer containing 10 mM DTT. The mevalonate kinase irreversibly lost all enzyme activity after freezing. The activity of rat mevalonate kinase was also sensitive to pH, and nearly all enzyme activity was lost when the pH was lower than 6.

TABLE I

Purification of Mevalonate Kinase From Rat Liver

| Purification Step | Total Protein (mg) | Total Units | Specific Activity (nmol/min/mg protein) | Fold Purification | % Recovery |
|---|---|---|---|---|---|
| 100,000 × g supernatant | 613 | 28.2 | 62.4 | — | 100 |
| 45% Ammonium Sulfate | 264 | 29.4 | 111.3 | 1.8 | 77 |
| Blue Sepharose | 19.7 | 24.2 | 1229 | 19.7 | 63 |
| 60% Ammonium Sulfate | 9.20 | 17.7 | 1925 | 30.8 | 46 |
| Sephadex G-150 | 1.35 | 8.58 | 6341 | 101.6 | 23 |
| ATP-Agarose | 0.23 | 7.28 | 31,667 | 507.0 | 19 |

EXAMPLE 5
Antibody to Rat Mevalonate Kinase

Antibody to mevalonate kinase was prepared in New Zealand White rabbits. Animals were injected subcutaneously with 50 µg of rat mevalonate kinase purified as described in Example 4 in an emulsion containing 0.25 mg/ml monophosphoryl lipid A, 0.25 mg/ml trehalose dimycolate, 2% squalene and 0.2% TWEEN 80 ™ (RIBI Immunochem Research, Hamilton, Mont.). After 4 weeks, the rabbits received another subcutaneous injection of 100 µg of mevalonate kinase, and 10 days later they were bled. IgG was purified from pre-immune and immune sera using a Protein-A affinity column as described in Goding, J. W., J. Immunol. Meth. 13, 215-226 (1976).

EXAMPLE 6
Isolation and DNA Sequence Analysis of a cDNA Clone Coding for Rat Mevalonate Kinase A lambda gt11 cDNA library derived from mRNA purified from the livers of rats treated with diets containing 5% cholestyramine and 0.1% lovastatin (Clarke, C. F. et al., Mol. Cell. Biol. 7, 3138-3146 (1987)) was screened for rat mevalonate kinase cDNA clones. Positive clones were identified by immunoscreening using the antibody described in Example 5 according to the method of Young, R. A. et al., Proc. Natl. Acad. Sci. USA 80, 1194-1198 (1983).

Three cDNA clones for rat mevalonate kinase (pMK 2, 9 and 10) were identified as positive clones after immunoscreening $4 \times 10^5$ recombinants from the cDNA expression library. The positive plaques so identified were removed from the agar plate and transferred to 1.0 ml of SM media (SM media=5.8 g NaCl, 2 g $MgSO_4.7H_2O$, 50 ml 1M Tris.HCl pH 7.5, 0.1% gelatin per liter). Large quantities of phage from the single plaques were prepared by mixing phage from the plaques with *Escherichia coli* Y1090 cells (Clontec Laboratories, Inc.) and agar and pouring this mixture onto plates. The agar plates were incubated at 37° C. for 4 to 6 hours, after which the phage were collected by centrifugation at $4000 \times g$ for 15 minutes at 4° C. The lambda DNA was purified by DEAE-cellulose chromatography (Helms, C. et al., Methods in Enzymology, Vol. 153, pgs. 69–82 (1987)). The cDNA inserts were then excised from the lambda vector by digesting 50 μg of lambda vector DNA with 20 units of Eco RI (Bethesda Research Laboratories, Gaithersburg, Md.) with 20 μl of high salt buffer (100 mM Tris-HCl, 50 mM NaCl, 10 mM $MgCl_2$, pH 7.5) in a total volume of 200 μl at 37° C. for 4 hours. The DNA in the digestion mixture was purified using sequential phenol, phenol-chloroform-isoamyl alcohol and chloroform-isoamyl alcohol extractions, ethanol precipitated, and dissolved in TE buffer (10 mM Tris-HCl, 1.0 mM EDTA, pH 8.0). The cDNA inserts were then isolated by separating them from the remaining lambda vector using agarose gel electrophoresis, cutting the bands containing the inserts from the agarose gel, and electroluting the cDNA inserts from the bands cut from the gel. The sizes of the cDNA inserts as determined by agarose gel electrophoresis ranged from 0.6 to 1.1 kb.

To obtain a full-length cDNA clone, the 1.1 kb cDNA insert from one of the clones (pMK 9) was radiolabelled by random priming to a specific activity of $10^9$ cpm/μg of DNA accordingly to the method of Feinberg, A. P. et al., Anal. Biochem. 132, 6–13 (1983). The radiolabelled probe was used to screen approximately $2 \times 10^5$ recombinants. Plaque hybridization was performed following standard high stringency procedures as described in Maniatis et al., Molecular Cloning: A Laboratory Manual, Cold Spring Harbor Laboratory, Cold Spring Harbor, N.Y. (1982), after which the filters were washed at 68° C. with $2 \times SSC$ ($1 \times SSC = 0.15M$ NaCl/0.015M sodium citrate, pH 7.0) containing 0.1% SDS, followed by washes with $0.1 \times SSC$ containing 0.1% SDS. Fifteen additional cDNA clones were plaque purified as described above after screening the cDNA library using the radiolabelled pMK 9 as a probe. Seven of these clones contained a cDNA insert of approximately 1.7 kb which was the largest cDNA isolated. The seven 1.7 kb cDNA Eco RI inserts were isolated as described above, and ligated into the Eco RI site of the multiple cloning site of the pGEM-3Z vector (Promega, Madison, Wis.) by incubating 0.3 μg of cDNA insert and 0.1 μg of pGEM-3Z vector at 15° C. for 1 hour in a total volume of 15 μl with buffer containing 40 mM Tris-HCl pH 7.5, 10 mM DTT, 0.5 mM ATP, 50 μg/ml BSA and 1 unit of $T_4$ DNA ligase. The ligation reaction was stopped with 2 μl of 0.5M EDTA, and the DNA was purified by phenol and phenol:chloroform extractions and collected by ethanol precipitation. DH5αF' host cells (Bethesda Research Laboratories) were transformed with these constructs according to the manufacturer's protocol, and the subclones were designated pMKZ 101–107. Large quantities of the construct DNA were prepared by growing large-scale liquid cultures of these subclones and extracting and purifying the DNA by the alkaline lysis method as described in Maniatis et al., *Molecular Cloning: A Laboratory Manual*, Cold Spring Harbor Laboratory, Cold Spring Harbor, N.Y. (1982). Restriction mapping was performed by digesting the purified DNA with either single restriction enzymes or with a combination of restriction enzymes and analyzing the digestion products by agarose gel electrophoresis. The seven 1.7 kb cDNA Eco RI inserts were also ligated into the Eco RI site of m13mp18 and m13mp19 vectors (BioRad, Richmond, Calif.) by incubation at 15° C. for 1 hour under the reaction conditions described above. These constructs were also used to transform DH5αF' cells according to the manufacturer's protocol. These subclones were designated pMK 101–107. Single-stranded DNA (for subclones pMK101 and pMK102) were generated in liquid cultures by these host cells and collected by centriguation. The single-stranded DNA was purified according to the manufacturer's protocol (BioRad, Richmond, Calif.) and sequenced using the dideoxy chain termination method of Sanger, F. et al., Proc. Nat'l Acad. Sci. USA 74, 5463–5467 (1977).

EXAMPLE 7

Isolation, DNA Sequence Analysis, and Deduced Amino Acid Sequence Analysis of a cDNA Clone Coding for Human Mevalonate Kinase To obtain the full length human mevalonate kinase cDNA clone, the insert from the full length rat mevalonate kinase cDNA (from subclone pMKZ101) was isolated as described in Example 6 and radiolabelled by random priming to a specific activity of $10^9$ cpm/μg of DNA according to the method of Feinberg, A. P., et al., Anal. Biochem. 132, 6–13 (1983). The radiolabelled probe was used to screen approximately $1 \times 10^6$ recombinants from a human skin fibroblast cDNA library in λgt11 purchased from Clontech Laboratories, Inc. Plaque hybridization was performed following standard high-stringency procedures described by Maniatis et al. in Molecular Cloning: A Laboratory Manual, Cold Spring Harbor Laboratory, Cold Spring Harbor, N.Y. (1982). The filters were then washed at 68° C. with $1 \times SSC$ ($1 \times SSC = 0.15M$ NaCl/0.015M sodium citrate, pH 7.0) containing 0.1% SDS, followed by washes with $0.1 \times SSC$ containing 0.1% SDS.

Nine cDNA clones coding for human mevalonate kinase were plaque purified as described in Example 6 after screening $1 \times 10^6$ recombinants from the human skin fibroblast cDNA library. The lambda DNA from these clones was extracted and purified from plate lysate preparations, digested with the restriction endonuclease Eco RI to release the cDNA insert, and the cDNA inserts isolated as described in Example 6. Four of these clones (λHMK1,4,7,9) contained a cDNA insert of approximately 2.0 kb which was the largest cDNA isolated. The EcoRI inserts from two of these clones (λHMK1 and λHMK4) were ligated into the Eco RI site of the multiple cloning site of the m13mp18 and m13mp19 vectors (BioRad, Richmond, Calif.) using the same ligation conditions as described in Example 6. These constructs were used to transform DH5αF' cells (Bethesda Research Laboratories) according to the manufacturer's protocol for DNA sequencing. These subclones were designated pHMK 1–4. Large scale liquid cultures of pHMK1 and pHMK4 were prepared and the single-stranded DNA was collected by centrifugation. The single stranded DNA was purified according to the manufacturer's protocol (BioRad, Richmond, Calif.) and sequenced using the dideoxy chain termination method of Sanger, F. et al., Proc. Nat'l. Acad. Sci. USA 74, 5463–5467 (1977). Sequencing reactions using the Klenow fragment of DNA polymerase I (New England BioLabs) or the modified T7 DNA polymerase (Sequenase, United States Biochemicals) were performed following the manufacturers' protocols. The DNA sequence was aligned using the Intelligenetics computer program, and the EMBL/GenBank and PIR databases were searched for homologies to the DNA and protein sequences of human mevalonate kinase.

The complete DNA sequence was determined, and the longest open reading frame of 1,187 bp coded for a protein containing 396 amino acids with a deduced molecular weight of 42,450. The deduced amino acid sequence of mevalonate kinase contained the Gly-X-Gly-X-X-Gly (X=any amino acid) site found in protein kinases.

DETAILED DESCRIPTION OF THE DRAWINGS

FIGS. 1A and 1B: Nucleotide sequence of the cDNA encoding human mevalonate kinase and the corresponding deduced amino acid sequence. The nucleotides have their usual single-letter designations (A, G, T or C) used routinely in the art. The 5'-untranslated nucleotide sequence extends from $-1$ to $-91$. The 1188 bp of coding sequence and the corresponding amino acid sequence starts at the first methionine, at position $+1$. The 3'-untranslated region begins at $+1189$ and extends to $+1881$ with a polyadenylation signal at $+1785$.

What is claimed is:

1. An isolated and purified nucleic acid selected from the group consisting of the nucleic acid of FIGS. 1A and 1B and a nucleic acid that is 100% complementary to the nucleic acid of FIGS. 1A and 1B.

* * * * *